United States Patent [19]

Murray-Shelley

[11] Patent Number: 5,145,647
[45] Date of Patent: Sep. 8, 1992

[54] AUTOCLAVES

[75] Inventor: Richard Murray-Shelley, Pontypridd, Wales

[73] Assignee: Smiths Industries Public Limited Co., London, England

[21] Appl. No.: 600,696

[22] Filed: Oct. 22, 1990

[30] Foreign Application Priority Data

Oct. 20, 1989 [GB] United Kingdom ............... 8923673

[51] Int. Cl.$^5$ .................................... G05B 19/00
[52] U.S. Cl. ...................... 422/116; 422/26; 422/295
[58] Field of Search ............. 422/26, 106, 295, 298, 422/107, 116; 368/110–113

[56] References Cited

U.S. PATENT DOCUMENTS

| | | | |
|---|---|---|---|
| 3,736,569 | 5/1973 | Bouricius et al. | 364/200 |
| 4,067,691 | 1/1978 | McGady et al. | 422/116 |
| 4,239,731 | 12/1980 | Gillis | 422/112 |
| 4,261,950 | 4/1981 | Bainbridge et al. | 422/116 |
| 4,594,685 | 6/1986 | Owens | 364/900 |
| 4,636,967 | 1/1987 | Bhatt et al. | 364/550 |
| 4,710,350 | 12/1987 | Petersen | 422/295 |
| 4,865,814 | 9/1989 | Childress | 422/116 |
| 4,908,188 | 3/1990 | Jefferis, III et al. | 422/111 |
| 4,942,559 | 7/1990 | Fleck et al. | 368/113 |
| 5,012,435 | 4/1991 | Bailey et al. | 364/569 |

FOREIGN PATENT DOCUMENTS

| | | |
|---|---|---|
| 0015328 | 9/1980 | European Pat. Off. . |
| 0028542 | 5/1981 | . |
| 0177119 | 4/1986 | . |
| 0177123 | 4/1986 | . |
| 0290929 | 11/1988 | . |
| 2052800 | 1/1981 | United Kingdom ............... 422/116 |
| 2207258 | 1/1989 | United Kingdom . |

OTHER PUBLICATIONS

Simpson, Robert E., *Introductory Electronics for Scientists and Engineers*, 1987, pp. 806–814.
Strargio, Christopher E., *Laboratory Experiments for the Microtrainer*, Jan. 1986, pp. 5-1 to 5-3.

Primary Examiner—Robert J. Warden
Assistant Examiner—Krisanne M. Thornton
Attorney, Agent, or Firm—Pollock, VandeSande and Priddy

[57] ABSTRACT

The pressurization period of an autoclave is controlled by an oscillator which provides an output to the autoclave control unit. The control unit has a microprocessor with its own clock. The number of times that a portion of the program is carried out by the microprocessor during the pressurization period of the autoclave, is counted into a register to decrease a separately established count in the register. This separately established count is representative of the correct operating time of the pressurization period. If, at the end of the pressurization period, the count in the register exceeds zero by more than an allowable error, a fault indication is produced on a display and the autoclave door is maintained locked so as to prevent access to articles in the autoclave.

10 Claims, 1 Drawing Sheet

AUTOCLAVES

This invention relates to autoclaves and methods of timing them.

Autoclaves are used for sterilization or other treatment of articles at elevated temperature in the presence of liquid vapor at elevated pressure. The articles to be treated are placed in a pressure vessel which includes a heater and a reservoir of liquid such as distilled water. In operation, the vessel is closed and the heater turned on so that the water is heated. The steam produced is allowed to vent from the vessel for a short time so as to flush air from the apparatus. The air vent is then closed so that pressure and temperature within the vessel increase to predefined levels. The atmosphere of high humidity and temperature in the vessel is sufficient to sterilize the articles after a predetermined time. When the sterilization cycle is complete, the heater is turned off and the vessel is allowed to cool, or is actively cooled such as by a fan. When the pressure in the vessel has dropped to a safe level, the door of the vessel is unlocked allowing the articles to be removed and other articles to be sterilized.

It is a requirement of autoclaves to ensure that the articles being treated are subjected to elevated temperature and pressure for the correct period of time. It is important to ensure that the timing of the pressurization phase is accurate and it is preferable to be able to provide an independent check of the timing of this period. This can lead to excessive expense and complication in the construction of the autoclave.

BRIEF SUMMARY OF THE INVENTION

It is an object of the present invention to provide an autoclave and a method of timing by which an independent check of the pressurizing period can be made.

According to one aspect of the present invention, there is provided a method of timing operation of an autoclave, comprising the steps of deriving from a first oscillator a first clock signal and using the first clock signal to time the duration of a pressurization period of the autoclave, deriving from a microprocessor having its own clock separate from the first oscillator a count of the number of times a portion of a program of the microprocessor has been executed during the pressurization period such that the count is representative of the duration of the pressurization period, and providing a fault indication when the count differs by more than a predetermined amount from a separately established count representative of the desired duration of the pressurization period.

The method preferably includes the steps of entering the separately established count as a predetermined number into a register and using the count of the number of times the portion of the program has been executed to reduce the number in the register, the fault indication being provided if the number in the register at the end of the pressurization period exceeds a predetermined value. The portion of the program may be one which is only executed during the pressurization phase and may be a temperature control algorithm. The fault indication may be provided on a visual display and may cause the autoclave to prevent access to articles within the autoclave.

According to another aspect of the invention there is provided an autoclave arranged to operate by a method according to the above one aspect of the present invention.

According to another aspect of the present invention there is provided an autoclave including a first oscillator arranged to derive a first clock signal, control means arranged to control the duration of a pressurization period of the autoclave in response to the first clock signal, the control means including a microprocessor and a clock source separate from the first oscillator which controls timing of a program in the microprocessor, means for counting the number of times a portion of the program has been executed during the pressurization period, and the control means being arranged to compare a first count of the number of times the portion of the program has been executed with a second count established independently, the control means being arranged to provide a fault indication when the second count differs by more than a predetermined amount from the first count.

The autoclave preferably includes a register, the first and second counts being subtracted from one another in the register. The autoclave may include a visual display, the fault indication being provided on the visual display. The autoclave may include a lock by which the door of the autoclave is locked, the fault indication being arranged to maintain the lock closed so as to prevent access to articles in the autoclave.

An autoclave for use in sterilization and its method of timing will now be described, by way of example, with reference to the accompanying drawings, in which:

DESCRIPTION OF THE PREFERRED EMBODIMENTS

Figure 1:
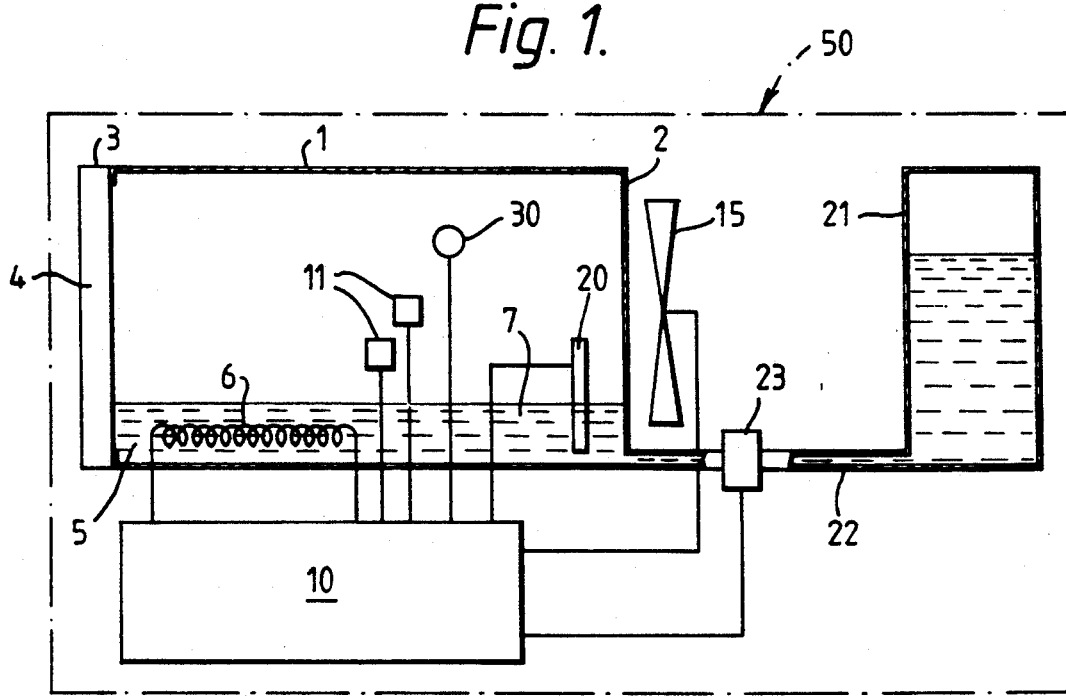
FIG. 1 is a schematic side elevation view of the autoclave.

With reference first to FIG. 1, the autoclave sterilizer comprises a cylindrical pressure vessel 1 that is closed at its rear end 2 and open at its front end 3. A door 4 is provided at the front end 3 which can be closed to seal the vessel 1 after insertion of the articles to be sterilized. The lower part of the vessel 1 provides a water reservoir 5 in which is located an electrical resistance heating filament 6 that is immersed in water 7. Current can be supplied to the filament 6 from a control unit 10. The reservoir 5 need not be within the pressure vessel 1 itself providing it opens into the pressure vessel.

A water level sensor 20 is mounted in the water reservoir 5 to indicate the level of water in the reservoir. The sensor 20 is of the conductivity kind having two electrodes exposed to any water in which the sensor is immersed. In this way, the resistance between the two electrodes falls when the level of conductive water reaches its full level and rises when the electrodes are exposed by a fall in the water level below the full level. An output from the sensor 20 is supplied to the control unit 10.

The sterilizer also includes a tank 21 external of the pressure vessel 1 which is connected with the reservoir 5 via tubing 22 and an electrically-operated valve 23. The valve 23 is controlled by the control unit 10 which also receives input signals from various sensors 11 in accordance with, for example, temperature and pressure.

Projecting through the wall of the vessel 1 there is a valve 30 which allows escape of air but shuts to allow a build up of pressure.

A cooling fan 15 is mounted outside the rear of the pressure vessel 1 which is arranged to blow air onto the vessel to promote cooling at the end of the sterilizing cycle. The pressure vessel 1 is contained within an outer housing 50 which is insulated from the pressure vessel 1 and which supports the various control switches and display panels, not shown.

In operation, articles to be sterilized are placed within the pressure vessel 1, the door 4 is closed and the sterilizer is turned on. This causes the water level sensor 20 to be checked by the control unit 10. If the control unit 10 sees a high resistance at the sensor 20 this indicates that the level of water in the reservoir 5 is low and thereby causes the control unit 10 to open the valve 23 and allow water from the tank 21 to flow along the tubing 22 into the reservoir 5. This continues until the sensor 20 gives a full level output. If no full level output is produced by the sensor 20 after a predetermined time, a fault is indicated by the unit 10 to show either that the tank 21 is empty or that the level sensor 20 is faulty.

Once the output of the sensor 20 has changed from a low to a full level output, the valve 23 is closed and the sterilizing/pressure cycle is started.

If, however, when the sterilizer is turned on, the output of the sensor 20 indicates a full level, a different sequence of operation is initiated. A full output from the sensor 20 may indicate either that the operative part of the sensor is immersed in water in the reservoir 5 and that the reservoir is therefore full, or that the operative part of the sensor is exposed above the level of water in the reservoir but that the operative part is wet as a result of water clinging to the sensor from the previous cycle. The reservoir 5 will normally need to be filled at the start of a cycle because water will have been lost during the preceding cycle. A full output from the sensor at the start of the cycle, therefore, is generally indicative of an exposed but wet sensor. It will be appreciated that if this full output is simply interpreted as an indication that the reservoir contains the correct amount of water, the sterilization cycle will be started with insufficient water. This will usually lead to the cycle aborting because of failure to reach the correct pressure and can result in damage to the heater 6. On the other hand, if the sensor output is ignored and the reservoir 5 is automatically filled from the tank 21 with extra water, this can lead to overfilling with the consequent danger that hot water will flood out the vessel 1 when the door 4 is opened.

The present invention reduces this risk by causing the heater 6 to be energized to warm the pressure vessel 1 and, more particularly, to warm the sensor 20 for a predetermined time. The amount of heating produced is less than during a normal pressure cycle, so that it is insufficient to cause damage if the heater 6 is exposed above the water, but is sufficient to promote drying of the sensor or any part of the sensor exposed above the water level. During this period, the valve 30 is open so that water evaporated from the sensor can escape. After the predetermined time, the output of the sensor 20 is rechecked by the control unit 10. If the output now indicates that there is a low water level, the valve 23 is opened to allow water from the tank 21 into the reservoir 5 in the manner described above. If, however, the output from the sensor 20 still indicates a high water level, the heater 6 is either reenergized or maintained energized for another predetermined period after which the output of the sensor 20 is checked again. This may be repeated several times after which, if the sensor still produces a full level output, a trial sterilization cycle is started. During this cycle, the pressure and temperature in the vessel 1 are monitored closely for any departure from normal behavior. If the cycle operates normally, it is continued as a full sterilization cycle. If some anomalous behavior is observed, the autoclave reverts to a safe state in which the heater is turned off, the door is maintained locked and a valve (not shown) is opened to exhaust pressure in the vessel 1 such as to the water tank 21.

In this way, the risk of the autoclave operating with insufficient water is minimized.

To ensure that articles are correctly sterilized it is important to ensure that they are maintained at a sufficiently high temperature and pressure for sufficient time. It is now a requirement in some countries that the timing of the sterilizing phase of operation of the autoclave be verified by a clock which is separate from the clock used for timing other routine timing functions in the autoclave. Examples of such routine timing functions are: the time control for the heater 6 to dry the chamber water level sensor 20, the timing of the valve 23 being open, the timing of an initial heating phase to determine if the heater 6 is functioning correctly, the timing of the drying cycle, and timing routines for the autoclave display, i.e. the frequency of flashing characters on the display.

Figure 2:
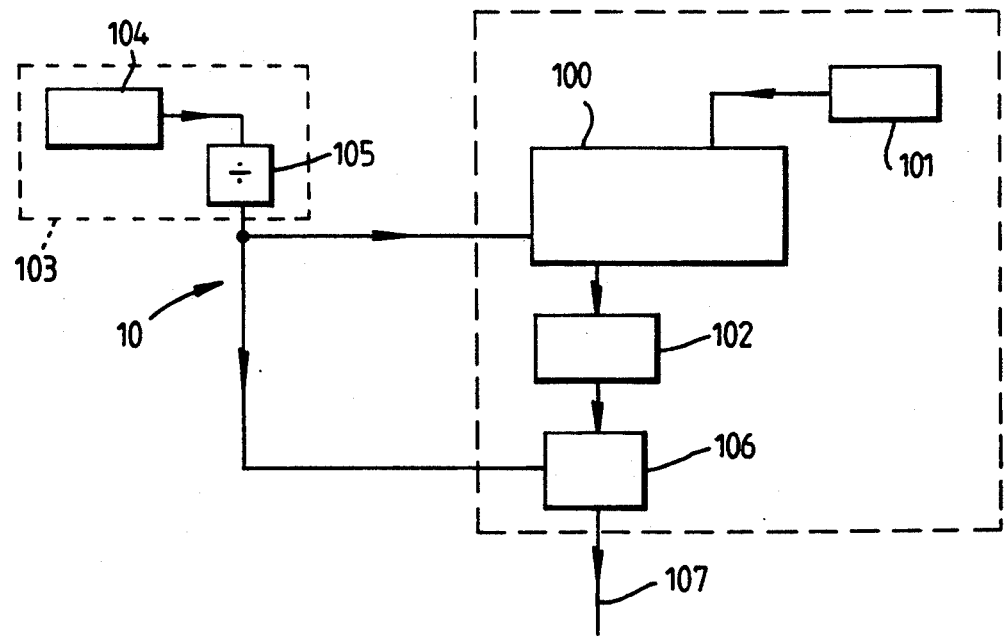
FIG. 2 illustrates operation of a part of the autoclave.

With reference to FIG. 2, the control unit 10 of the autoclave includes a 128 bytes RAM type 6802 microprocessor 100 having its own clock 101 derived from a 3.2768 MHz crystal. The software of the microprocessor 100 counts the number of times that a certain portion of the program is executed. The portion of the program which is counted is one which is only performed during the pressurization/sterilization phase, which is the only time during which dual timing is needed. In this particular example, it is a proportional temperature control algorithm which is counted but other portions of the program which are performed during the pressurization phase could alternatively be counted. This count is directly related to the frequency of the clock 101 and the duration of the pressurization period. The portion of the program counted takes approximately 0.8 s to perform, thus, for a standard 134 C cycle taking 200 s, the count would be approximately 250. The expected number of counts for a correct duration period, i.e. 250, is separately established and entered in a register 102 before the start of the pressurization period and this number is reduced by one each time that the relevant portion of the program is executed.

The control unit 10 also includes a separate oscillator 103 having a crystal 104 running at 32.768 KHz which produces a fundamental divided frequency of 200 Hz. The oscillator 103 is used to control the pressurization/sterilization cycle time by dividing a fundamental frequency at 105 to produce accurate 0.5 s intervals. The output from divider 105 is supplied to the microprocessor 100, for use in timing the sterilization phase. At the end of the pressurization phase, a comparator 106 is triggered to check that the contents of the register 102 reads 0 to within a predetermined allowable error. If the contents of the register 102 differs by more than a predetermined amount from this 0 reading, a fault indication is produced in the form of an output on line 107. This causes an indication to be produced on a visual display (not shown) and causes the autoclave to revert to a safe state. More particularly, the door lock of the autoclave is maintained closed to prevent access to the articles in the autoclave which will not have been fully sterilized. Various other, similar ways of timing the operation of the autoclave are possible. For example, the count of the number of times the portion of the program is executed could be entered in one register and the separately established count representative of the desired duration of the pressurization period entered in a different register. At the end of the pressurization period, as controlled by the oscillator 103, the contents of the two registers would be checked and a fault indication provided if they differ by more than a predetermined amount.

What I claim is:

1. A method of timing operation of an autoclave comprising the steps of: generating a first clock signal from a first oscillator; controlling with the first clock signal the duration of a pressurization period of the autoclave; counting in a microprocessor having its own clock separate from the first oscillator a first count of the number of times a portion of a program of the microprocessor has been executed during the pressurization period such that the first count is representative of the duration of the pressurization period; generating separately a second count representative of the desired duration of the pressurization period; and generating a fault signal when the first count differs by more than a predetermined amount from the second count.

2. A method according to claim 1 including the steps of: entering the second count as a predetermined number into a register; reducing the number in the register by the first count; and generating said fault signal if the number in the register at the end of the pressurization period exceeds a predetermined value.

3. A method according to claim 1, wherein the said portion of the program is one which is only executed during the pressurization phase.

4. A method according to claim 3, wherein the said portion of the program is a temperature control algorithm.

5. A method according to claim 1 wherein the autoclave includes a visual display, and wherein said fault signal is supplied to the visual display and provides a representation of the fault on said display.

6. A method according to claim 1, wherein the generation of said fault signal prevents access to articles within the autoclave.

7. An autoclave comprising a pressure chamber and a control unit that controls the duration of a pressurization period of the pressure chamber, the control unit including: a first oscillator, said first oscillator generating a first clock signal that controls the duration of the pressurization period; a microprocessor; a clock source separate from said first oscillator for controlling timing of a program in said microprocessor; means for counting as a first count the number of times a portion of said program has been executed during the pressurization period; means for storing a second count representative of the desired duration of the pressurization period; means for comparing the first count with the second count; and means for generating a fault signal when the second count differs by more than a predetermined amount from the first count.

8. An autoclave according to claim 7 wherein the means for storing the second count is a register in said control unit, and wherein the autoclave includes means for subtracting the first and second counts from one another.

9. An autoclave according to claim 7, including a visual display, and wherein the control unit supplies said fault signal to the visual display.

10. An autoclave according to claim 7, wherein the pressure chamber of the autoclave has a door, and wherein the control unit maintains the door locked on occurrence of the fault signal so as to prevent access to articles in the autoclave.

* * * * *